US00PP23539P2

(12) United States Plant Patent
Smith

(10) Patent No.: US PP23,539 P2
(45) Date of Patent: Apr. 16, 2013

(54) ***CHRYSANTHEMUM* PLANT NAMED 'SYEMA ORANBI'**

(50) Latin Name: *Chrysanthemum×morifolium*
Varietal Denomination: Syema Oranbi

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 260 days.

(21) Appl. No.: 13/065,480

(22) Filed: Mar. 23, 2011

(51) Int. Cl.
*A01H 5/00* (2006.01)

(52) U.S. Cl. ..... Plt./287

(58) Field of Classification Search ..... Plt./287, Plt./289, 290
See application file for complete search history.

*Primary Examiner* — Kent L Bell
(74) *Attorney, Agent, or Firm* — Joshua L. Price

(57) ABSTRACT

A new *Chrysanthemum* plant named 'Syema Oranbi' particularly distinguished by the large, yellow and orange bi-colored inflorescences, dark yellow-green foliage, nicely mounded plant habit, with a natural flowering season of about mid-October.

1 Drawing Sheet

Latin name of the genus and species of the plant claimed: *Chrysanthemum×morifolium.*

Varietal denomination: 'Syema Oranbi'.

BACKGROUND OF THE NEW PLANT

The present invention comprises a new *Chrysanthemum*, botanically known as *Chrysanthemum×morifolium*, and hereinafter referred to by the variety name 'Syema Oranbi'.

'Syema Oranbi' is a product of a planned breeding program. The new cultivar has large, yellow and orange bi-colored inflorescences, dark yellow-green foliage, nicely mounded plant habit, with a natural flowering season of about mid-October.

'Syema Oranbi' originated as a natural whole plant mutation of 'Empire Emma', U.S. Plant Pat. No. 20,196. 'Syema Oranbi' was discovered and selected by the inventor as a single flowering plant within a population of the parent cultivar in a controlled breeding program in Alva, Fla. in November 2007. The parent cultivar 'Empire Emma' has larger inflorescences with less orange color in the inflorescence, little larger plant habit, and a natural flowering season that is a little faster.

The first act of asexual reproduction of 'Syema Oranbi' was accomplished when vegetative cuttings were propagated from the initial selection in December 2007 in a controlled environment in Alva, Fla.

BRIEF SUMMARY OF INVENTION

Horticultural examination of plants grown from cuttings of the plant initiated in December 2007, and continuing thereafter, has demonstrated that the combination of characteristics as herein disclosed for 'Syema Oranbi' are firmly fixed and are retained through successive generations of asexual reproduction.

'Syema Oranbi' has not been observed under all possible environmental conditions. The phenotype may vary significantly with variations in environment such as temperature, light intensity and day length.

A Plant Breeder's Right for this cultivar was applied for in Canada on Apr. 9, 2010 (No. 10-6930). 'Syema Oranbi' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syema Oranbi' with colors being as true as possible with an illustration of this type. The photographic drawing shows a flowering potted plant of the new variety.

DETAILED BOTANICAL DESCRIPTION

The plant used for the photographs were about 16 weeks old, grown in Monroeville, N.J., in an outdoor trial. Rooted cutting were grown in a nine inch pot with no terminal pinching of the apices. The photograph was taken in mid-October 2010 in New Jersey.

The plant descriptions and measurements were taken in Gilroy, Calif. in May 2010 under natural light. Plants were grown in 4.5 inch pots, under conditions which approximate those generally used for potted *Chrysanthemum* trials in a greenhouse. These plants used in the descriptions were about 10 weeks old.

Color references are made to The Royal Horticultural Society Colour Chart (R.H.S.) 2001.

TABLE 1

DIFFERENCES BETWEEN THE NEW VARIETY 'SYEMA ORANBI' AND A SIMILAR VARIETY

| | 'Syema Oranbi' | 'Iduna' (U.S. Plant Pat. No. 14,925) |
|---|---|---|
| Inflorescence size: | Larger | Smaller |
| Inflorescence color: | More orange | More bronze |

TABLE 1-continued

DIFFERENCES BETWEEN THE NEW VARIETY 'SYEMA ORANBI' AND A SIMILAR VARIETY

| | 'Syema Oranbi' | 'Iduna' (U.S. Plant Pat. No. 14,925) |
|---|---|---|
| Plant habit size: | Smaller with rounder habit | Larger, less round |
| Natural flowering season response: | Few days slower | Few days faster |
| Natural flowering response in shade: | About 10 days slower | About 10 days faster |

Plant:

*Form, growth and habit.*—Herbaceous decorative garden-type, stems upright, freely branching, strong and moderately vigorous growth habit.

*Plant height.*—15-16 cm.

*Plant height (inflorescence included).*—21-23 cm.

*Plant width.*—18-20 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A.

*Lower surface.*—Closest to RHS 137A.

*Mature, leaf color, upper surface.*—Closest to RHS 147A.

*Lower surface.*—Closest to RHS 137A.

*Length.*—4.5-4.7 cm.

*Width.*—3.5-3.7 cm.

*Shape.*—Ovate.

*Base shape.*—Attenuate.

*Apex shape.*—Mucronulate.

*Margin.*—Irregularly lobed; slightly palmate; serrate.

*Texture, upper surface.*—Bifid T-shaped hairs.

*Lower surface.*—Bifid T-shaped hairs.

*Color of veins, upper surface.*—RHS 138B.

*Color of veins, lower surface.*—RHS 138B.

*Petiole color.*—RHS 138B.

*Length.*—1.5-1.6 cm.

*Diameter.*—0.2 cm.

*Texture.*—Bifid T-shaped hairs.

Stem:

*Quantity of main branches per plant.*—5-6.

*Color of stem.*—Closest to RHS 146A.

*Length of stem.*—12-15 cm.

*Diameter.*—0.5 cm.

*Length of internodes.*—0.8-1.5 cm.

*Texture.*—Bifid T-shaped hairs.

*Color of peduncle.*—Closest to RHS 146A.

*Length of peduncle.*—4.0-8.0 cm.

*Peduncle diameter.*—0.15-0.2 cm.

*Texture.*—Bifid T-shaped hairs.

Inflorescence:

*Type.*—Compositae type, solitary inflorescences, decorative-type, borne terminally above foliage, ray florets arranged acropetally on a capitulum.

*Quantity of short days to flowering (response time).*—Approximately 58 days.

*Quantity of inflorescences per plant.*—10 fully open; 30 immature and numerous buds.

*Lastingness of individual blooms on the plant.*—About 5 weeks from the first color.

*Fragrance.*—Slightly spicy.

Bud (just when opening/showing color):

*Color.*—Closest to RHS 169A to RHS 169B.

*Length.*—1.0-1.2 cm.

*Width.*—1.1-1.2 cm.

*Shape.*—Oblate.

Immature inflorescence:

*Diameter.*—5.0-5.5 cm.

*Color of ray florets, upper surface.*—RHS 163B overlaid with RHS 19B to RHS N163A.

*Lower surface.*—RHS 164B base with hints of RHS 164A and RHS N163B.

Mature inflorescence:

*Diameter.*—6.5-7.5 cm.

*Depth.*—2.0 cm.

*Total diameter of 'disc'.*—0.3-0.4 cm.

*Receptacle height.*—0.4 cm.

*Receptacle diameter.*—0.7 cm.

Ray florets:

*Average quantity of florets.*—250 in numerous whorls.

*Color of florets, upper surface.*—RHS 15B overlaid with a hint of RHS 25B.

*Lower surface.*—Close to RHS 15D base; RHS 24D.

*Length.*—2.9-3.3 cm.

*Width.*—0.6-0.9 cm.

*Shape.*—Elliptical.

*Apex shape.*—Obtuse to rounded.

*Margin.*—Entire.

*Texture, upper surface.*—Papillose.

*Lower surface.*—Papillose.

Disc florets:

*Average quantity of florets.*—24-27.

*Color of florets.*—RHS 1C with RHS 3A apex.

*Length.*—0.5 cm.

*Width.*—0.1 cm.

*Shape.*—Tubular, elongated.

*Apex shape.*—Acute, 5 pointed.

Phyllaries:

*Quantity.*—Approximately 25.

*Color, upper surface.*—RHS 137A.

*Lower surface.*—Between RHS 147A and RHS 137A.

*Length.*—0.4-0.5 cm.

*Width.*—0.1-0.15 cm.

*Shape.*—Lanceolate.

*Apex shape.*—Acute.

*Base.*—Fused.

*Margins.*—Entire, papery.

*Texture, upper surface.*—Smooth.

*Lower surface.*—Bifid T-shaped hairs.

Reproductive organs:

*Pistil.*—1.

*Length.*—0.3-0.4 cm.

*Style color.*—RHS 1B.

*Style length.*—0.25-0.3 cm.

*Stigma color.*—RHS 6A.

*Stigma shape.*—Bi-parted.

*Ovary color.*—Not observed.

*Stamens.*—1.

*Color of filaments.*—RHS 155A.

*Length filaments.*—0.3 cm.

*Anther color.*—RHS 9B.

*Anther length*.—0.1 cm.
*Anther shape*.—Oval.
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Syema Oranbi' substantially as illustrated and described herein.

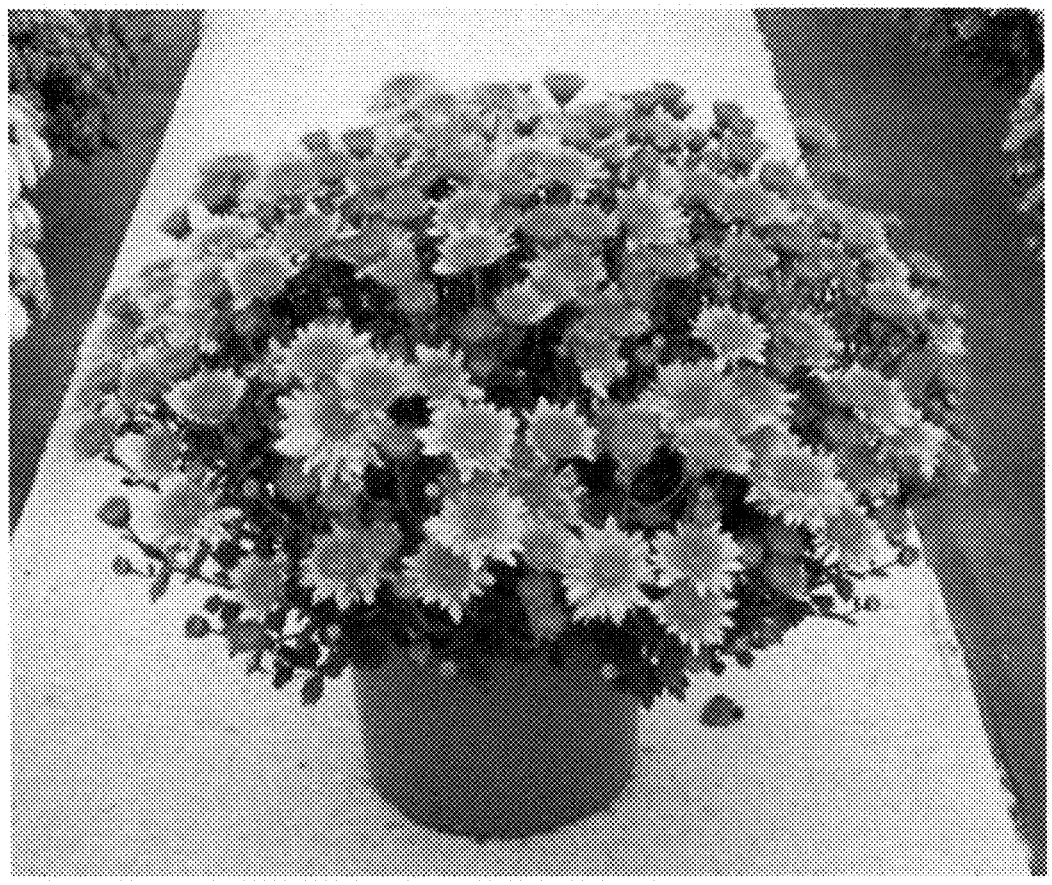

* * * * *